United States Patent
Chu et al.

(10) Patent No.: US 9,840,798 B2
(45) Date of Patent: Dec. 12, 2017

(54) THIN FILM METALLIC GLASS COATED NEEDLE

(71) Applicant: National Taiwan University of Science and Technology, Taipei (TW)

(72) Inventors: Jinn Chu, Taipei (TW); Yusuke Tanatsugu, Taipei (TW); Chia-Chi Yu, Taipei (TW); Chia-Lin Li, Taipei (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 150 days.

(21) Appl. No.: 14/919,749

(22) Filed: Oct. 22, 2015

(65) Prior Publication Data
US 2016/0331365 A1 Nov. 17, 2016

(30) Foreign Application Priority Data
May 15, 2015 (TW) .............................. 104115493 A

(51) Int. Cl.
*B32B 15/00* (2006.01)
*D05B 85/12* (2006.01)
*A61B 17/06* (2006.01)
*A61M 5/32* (2006.01)
*A61B 17/00* (2006.01)

(52) U.S. Cl.
CPC ........ *D05B 85/12* (2013.01); *A61B 17/06066* (2013.01); *A61B 2017/0084* (2013.01); *A61B 2017/00526* (2013.01); *A61M 5/329* (2013.01)

(58) Field of Classification Search
None
See application file for complete search history.

(56) References Cited

U.S. PATENT DOCUMENTS

| | | | |
|---|---|---|---|
| 3,356,047 A * | 12/1967 | Short | D05C 15/00 112/222 |
| 6,238,686 B1 * | 5/2001 | Burrell | A01N 59/16 424/423 |
| 7,906,219 B2 | 3/2011 | Ohara et al. | |

(Continued)

FOREIGN PATENT DOCUMENTS

| CN | 1938442 A | 3/2007 | |
|---|---|---|---|
| EP | 2392690 | * 12/2011 | C23C 14/14 |

(Continued)

OTHER PUBLICATIONS

W. Lyle McClung, S. Christopher Daniel, Walter McGregor, John G. Thacker, George T. Rodeheaver, and Richard F. Edlich, "Enhancing needle durability by silicon coating of surgical needles". The Journal of Emergency Medicine, vol. 13, No. 4, pp. 515-518, 1995.

(Continued)

*Primary Examiner* — Seth Dumbris
(74) *Attorney, Agent, or Firm* — CKC & Partners Co., Ltd.

(57) ABSTRACT

A thin film metallic glass coated needle includes a needle body, a needle head and a thin film metallic glass in amorphous structure and formed on a surface of the needle head and a surface of the needle body to reduce a surface energy and coefficient of friction. The thin film metallic glass is a titanium based comprising 35-45 at % titanium, 5-15 at % zirconium, 32-42 at % copper, 1-11 at % niobium and 2-12 at % cobalt.

6 Claims, 4 Drawing Sheets

(56) References Cited

U.S. PATENT DOCUMENTS

| | | | |
|---|---|---|---|
| 2002/0162605 A1* | 11/2002 | Horton, Jr. | A61B 17/866 148/304 |
| 2004/0042017 A1 | 3/2004 | Cohen et al. | |
| 2008/0202649 A1* | 8/2008 | Guo | C22C 14/00 148/561 |
| 2012/0189866 A1* | 7/2012 | Chu | B32B 7/12 428/615 |
| 2015/0053312 A1 | 2/2015 | Chu | |

FOREIGN PATENT DOCUMENTS

| | | | | |
|---|---|---|---|---|
| JP | 04065559 | * | 3/1992 | D04B 15/38 |
| JP | 2000160308 | * | 6/2000 | C22C 45/10 |

OTHER PUBLICATIONS

Yukio Inokuti, Hirotaro Mori. "Development of new patient-friendly therapeutic puncture needlewith high insulation and good adhesion". Journal of Materials Processing Technology, vol. 171, pp. 423-427, 2006.

* cited by examiner

THIN FILM METALLIC GLASS COATED NEEDLE

RELATED APPLICATIONS

This application claims priority to Taiwan Application Serial Number 104115493, filed May 15, 2015, which is herein incorporated by reference.

BACKGROUND

Field of Invention

The present invention relates to a thin film metallic glass. More particularly, the present invention relates to a thin film metallic glass for coating.

Description of Related Art

Metal, ceramic and polymer materials are widely used in our daily life. The implementation of metallic materials occupies the highest percentage. In comparison with polymer or composite materials, metallic materials have better physical resistance. Furthermore, metallic materials have longer researching history, and therefore the technique of associated fields is more mature and well developed. They can be found everywhere in a variety of products.

Common metallic material, for example, nano titanium aluminium nitride film, which shows high hardness, is used to improve the wear resistance of a product. Silicon titanium film is used to enhance the thermal stability of product at high temperature. Nano silicon titanium aluminium helium film is applied to increase anti-oxidation temperature. However, conventional metallic materials are mostly crystalline with limited malleability and therefore fail to satisfy product requirement in certain industry. For example, in terms of medical needle and industrial dispensing tip, the frequency of contacting is high.

Industrial dispensing tip can be found in many applications. Although the size of tip and glue material may be different, the difficulties encountered are usually related to the residue glue on the tip surface, leading to process interruption for clearance.

Lubricant is used on medical needle to reduce the friction between skin and the needle. However, in aesthetic or plastic surgery, the needle may be repeatedly used to tens or hundreds of times. After the heavy use, the friction between needle and skin may increase because lubricant dries out. The needle head will be blunt along the time course, such that the pain will be more pronounced to the recipient. The entire process may be affected accordingly.

Stitching needle, injection needle or aesthetic needle is disposable medical appliance. However, take stitching needle for example. Clinically, when using stitching needle to handle the wound, the duration and area may be long and broad, such that the needle head may become blunt, causing difficulty in operation. When it comes to injection needle, it is used for multiple times a day, for example, insulin injection taking 4-6 times a day. According to some researches, in the second attempt to use the same injection needle for insulin injection, the needle has been blunted. At the sixth attempt in injection, it is clear that the needle head has deformed.

Conventional needle head protection is achieved by using silicon nitride hard coating ($SiN_x$) with a thickness of about 500 nm. However, in order to improve the adhesion of the ceramic hard coating, another silicon oxynitride ($SiN_xO_y$) layer, which is approximately 500 nm in thickness, is introduced between the silicon nitride hard coating and the stainless steel. Although the coefficient of friction can be reduced and so as the friction resistance, the overall thickness can reach to 1000 nm, and the wound can be too large to recover.

Unlike the abovementioned metallic coating, thin film metallic glass exhibits random atomic arrangement and therefore exhibiting unique properties. For example, thin film metallic glass exhibits high hardness, superior fatigue resistance, low surface roughness, good wear resistance, and anti-bacterial properties. Thus, thin film metallic glass shows great potential in medical application.

SUMMARY

The instant disclosure provides a thin film metallic glass coating on a surface of a needle body and a surface of a needle head so as to reduce surface roughness and coefficient of friction. The hardness of the needle head can be increased by coating with thin film metallic glass. The thin film metallic glass is less likely to stick or be stuck on other materials. The durability of the needle is greatly promoted.

According to some embodiments of the instant disclosure, a thin film metallic glass coated needle includes a needle body, a needle head and a thin film metallic glass in amorphous structure and formed on a surface of the needle head and a surface of the needle body to reduce the surface energy, coefficient of friction, surface roughness, and simultaneously increase the hardness of the needle head.

According to some embodiments of the instant disclosure, the thin film metallic glass is a titanium-based thin film metallic glass comprising of 35-45 at. % titanium, 5-15 at. % zirconium, 32-42 at. % copper, 1-11 at. % niobium and 2-12 at. % cobalt.

According to some embodiments of the instant disclosure, the thin metallic glass film has a chemical formula of $Ti_{40}Zr_{10}Cu_{37}Nb_7Co_7$.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
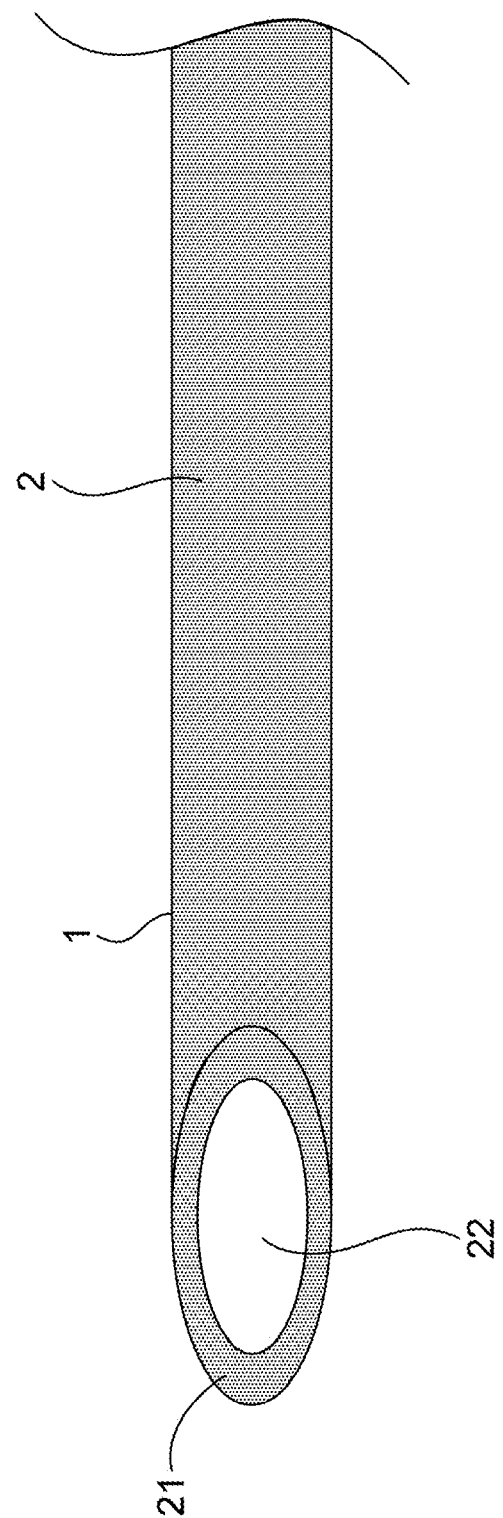
FIG. 1 is a schematic diagram showing a thin film metallic glass coated needle in accordance with an embodiment of the instant disclosure.

Reference will now be made in detail to the present embodiments of the invention, examples of which are illustrated in the accompanying drawings. Wherever possible, the same reference numbers are used in the drawings and the description to refer to the same or like parts.

Please refer to FIG. 1, showing a thin film metallic glass coated needle in accordance with an embodiment of the instant disclosure. As shown in FIG. 1, the thin film metallic glass (TFMG) 1 is an amorphous material and is formed on a surface of the needle body 2 and a surface of the needle head 21 of the needle body 2 so as to reduce the interfacial friction and surface roughness and increase the hardness of the needle head. In addition, in another embodiment of the instant disclosure, the needle body 2 has a needle tube 22. The inner surface of the needle tube 22 is coated with the thin film metallic glass 1. The thin film metallic glass 1 is a titanium-based thin film metallic glass. The thin film metallic glass 1 comprising 35-45 at. % titanium, 5-15 at. % zirconium, 32-42 at. % copper, 1-11 at. % niobium and 2-12 at. % cobalt. It should be noted that nickel cannot be used as an ingredient in the titanium-based thin film metallic glass because nickel can easily induce allergic response to living organisms and is poisonous to human body.

The material of needle body 2 is selected from a system consisting of titanium, titanium alloy, aluminium, aluminium alloy, copper, copper alloy, iron, iron alloy, gold, gold alloy and steel. In an embodiment of the instant disclosure, the thin film metallic glass 1 has a chemical formula of $Ti_{40}Zr_{10}Cu_{37}Nb_7Co_7$. The hardness of the thin metallic glass film 1 is greater than 700 HV, and a thickness of the thin film metallic glass 1 ranges from 50 to 200 nm. The titanium thin film metallic glass 1 is formed on the needle head 21 by vacuum sputtering system.

Figure 2:
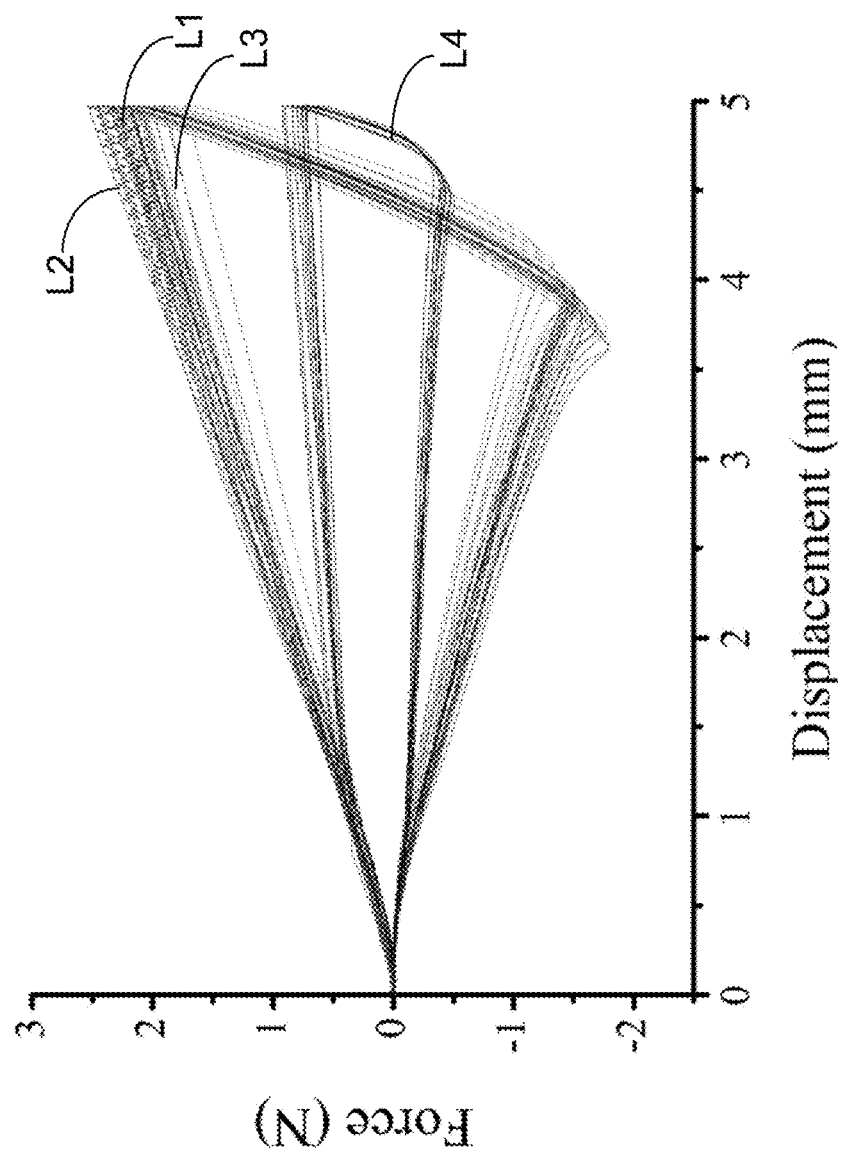
FIG. 2 is a insertion and extraction force analysis graph for needles with different coatings.

Hereafter will discuss empirical data of the thin film metallic glass 1 in various tests. Please refer to FIG. 2, showing an insertion and extraction force analysis graph for needles with different coatings. As shown in FIG. 2, in the puncturing test, different materials are used in parallel for comparison. Different coatings are formed on stainless steel needle head, and their puncturing forces are measured on the PU rubbers. L1 indicates uncoated needle head, L2 indicates pure titanium coated needle head, L3 indicates titanium nitride coated needle head, and L4 indicates the titanium based thin film metallic glass coated needle head in accordance with an embodiment of the instant disclosure. Y axis shows the puncturing force in Newton (N), while X axis shows the puncturing distance in millimetre (mm).

The uncoated needle head has an insertion force of about 2.3 N and a friction force of about 1.5 N, the pure titanium coated needle head has an insertion force of about 2.3 N and a friction force of about 1.6 N, the titanium nitride coated needle head has an insertion force of about 2.1 N and a friction force of about 1.5 N, and the titanium-based thin film metallic glass coated needle head has an insertion force of about 0.8 N and a friction force of about 0.3 N. The insertion force is obtained from the peak force during insertion and the friction force is obtained from peak force during extraction. Comparing the uncoated needle head and the titanium-based thin film metallic glass coated needle head, the insertion force reduces from 2.3 N to 0.8N. The friction force reduction is significant in comparison with other coatings, for example, the pure titanium or titanium nitride coating. Pure titanium and titanium nitride film are in crystalline structure, and they do not show significant improvement in friction reduction. The titanium-based thin film metallic glass shows a great decrease in insertion force because its amorphous structure provides a flatter surface, and therefore it is beneficial for medial injection or operation with multiple entries.

Figure 3:
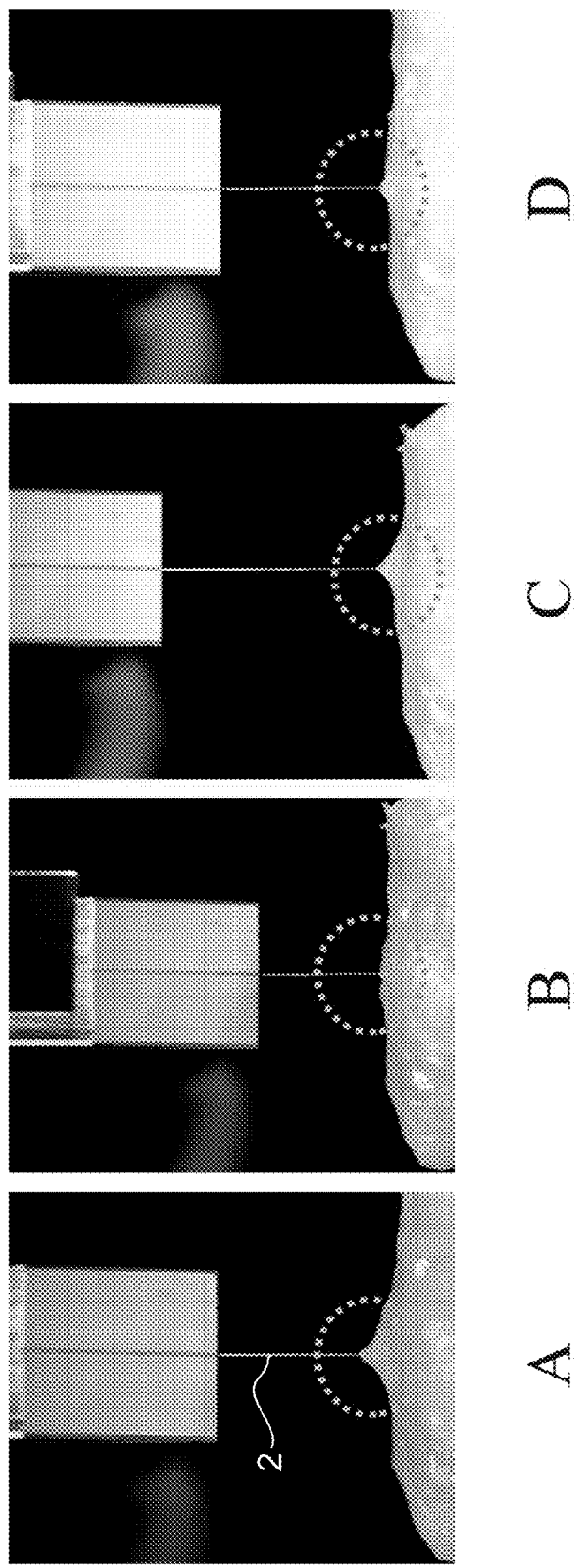
FIG. 3 are photos showing a puncturing tests for needles with different coatings.

Please refer to FIG. 3, showing puncturing tests for needles with different coatings. As shown in FIG. 3, in the puncturing test, different coating materials formed on the stainless steel needle head are tested on warm swine meat. A to D indicate uncoated needle head, titanium based thin film metallic glass coated needle head, pure titanium hard film coated needle head and titanium nitride coated needle head, respectively. The insertion force and friction force of these samples are as follows. The uncoated needle head has an insertion force of about 0.15 N and a friction force of about 0.044 N, the pure titanium coated needle head has an insertion force of about 0.16 N and a friction force of about 0.039 N, the titanium nitride coated needle head has an insertion force of about 0.14 N and a friction force of about 0.034 N, and the titanium-based thin film metallic glass coated needle head has an insertion force of about 0.08 N and a friction force of about 0.026 N.

When the needle head leaves the swine meat tissue, the titanium-based thin film metallic glass coated needle head shows less tissue sticking in comparison with uncoated or other coating materials. In addition, after the needle head is coated with titanium-based thin film metallic glass, it only requires half the force to enter the same depth in the swine meat. The pain felt by the recipient when the muscles are stretched is reduced, the durability of the needle is improved and the tissue is less likely to stick on the needle surface.

Figure 4:
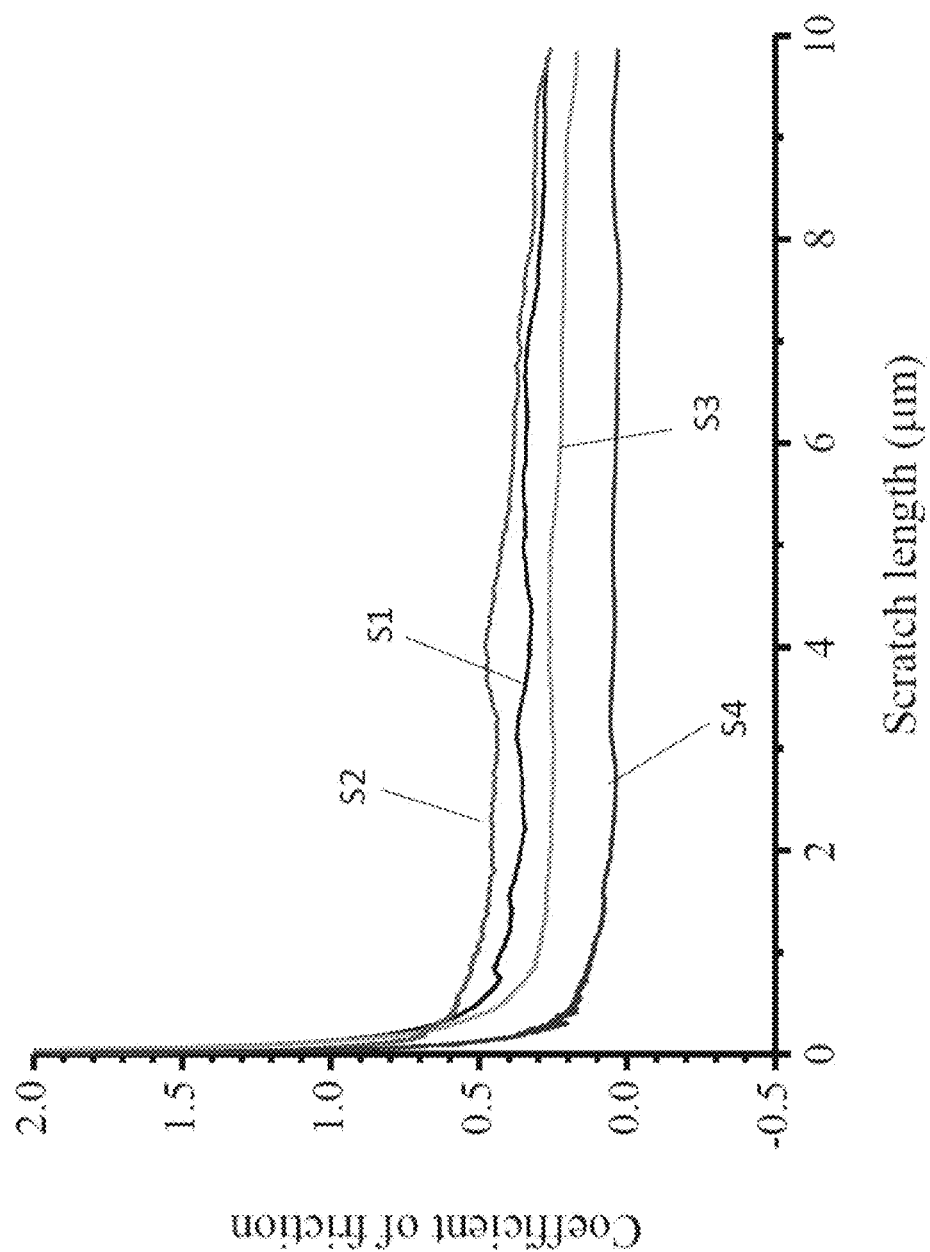
FIG. 4 is a coefficient of friction measurement graph for needles with different coatings.

Please refer to FIG. 4, showing coefficient of friction measurement graph for needles with different coatings. As shown in FIG. 4, in the coefficient of friction measurement, different coating materials go through diamond indenter for scratching test. S1 indicates uncoated needle head, S2 indicates pure titanium coated needle head, S3 indicates titanium nitride coated needle head, and S4 indicates the titanium-based thin film metallic glass coated needle head in accordance with an embodiment of the instant disclosure. Y axis shows the coefficient of friction, while the X axis shows the length of the scratching in μm.

The uncoated needle head has a coefficient of friction about 0.36, the pure titanium coated needle head has a coefficient of friction about 0.39, the titanium aluminium nitride coated needle head has a coefficient of friction about 0.23, and the titanium-based thin film metallic glass coated needle head has a coefficient of friction about 0.07. After coating with titanium-based thin film metallic glass, the coefficient of friction reduces from 0.36 to 0.07. In comparison with other coatings, the pure titanium or nitride titanium, the titanium-based thin film metallic glass has distinctive result. The crystalline titanium and titanium nitride ceramic hard coatings do not show significant reduction in coefficient of friction of stainless steel needle head surface. In contrast, the titanium-based thin film metallic glass greatly reduces coefficient of friction because of its amorphous structure. The amorphous structure has a surface that is flatter than the other crystalline films, and the amorphous structure also has a lower surface energy. As a result, in a puncturing test, the required insertion and extraction forces reduce and the sticking problem is minimized.

Please refer to Table 1, showing surface energy of different materials from a contact angle measurement. As shown in Table 1, the uncoated needle head has a surface energy of 39.8 mN/m, the pure titanium coated needle head has a surface energy of 37.2 mN/m, the titanium nitride coated needle head has a surface energy of 33.1 mN/m, and the titanium-based thin film metallic glass coated needle head has a surface energy of 26.9 mN/m. After coating with titanium-based thin film metallic glass, the surface energy reduces from 39.8 mN/m to 26.9 mN/m in relation of the uncoated needle head. In comparison with other coating film, for example, the pure titanium or nitride titanium, the titanium based thin film metallic glass has distinctive result. The crystalline pure titanium and the titanium nitride ceramic hard films do not show significant reduction in stainless steel needle head surface energy. In contrast, the titanium-based thin film metallic glass greatly reduces surface energy because of its amorphous structure. The amorphous structure has a surface that is flatter than the other crystalline films, and the amorphous structure also has a lower surface energy. As a result, in a puncturing test, the required insertion and extraction forces reduce and the sticking problem is minimized.

TABLE 1

| Film | Uncoated | TFMG | Titanium Nitride | Pure Titanium |
|---|---|---|---|---|
| Surface Energy (mN/m) | 39.8 | 26.9 | 33.1 | 37.2 |

According to the above empirical results, the titanium-based thin film metallic glass 1 has a chemical formula, $Ti_{40}Zr_{10}Cu_{37}Nb_7Co_7$, can reduce needle head surface friction and roughness, increase the hardness of the needle head and effectively minimize tissue sticking, and therefore the durability of the needle is greatly improved. In addition, the titanium-based thin film metallic glass can protect the needle head from blunting in repeatedly use. The pain to the recipient can be reduces altogether.

The metallic glass film 1 is an amorphous structure formed on the surface of the needle body 2 and a surface of the needle head 21 of the needle body 2 to reduce a surface energy, coefficient of friction and surface roughness. At the same time the titanium-based thin film metallic glass coated needle is less likely to stick to the other subjects. The overall durability and anti-bacterial properties are improved.

Although the present invention has been described in considerable detail with thereof, other embodiments are possible. Therefore, the spirit and scope reference to certain embodiments of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A medical injection needle coated with a thin film metallic glass, comprising:
   a needle body;
   a needle head; and
   a thin film metallic glass being of amorphous structure and formed on a surface of the needle head and a surface of the needle body, wherein the thin film metallic glass is a titanium-based thin film metallic glass comprising 35-45 at. % titanium, 5-15 at. % zirconium, 32-42 at. % copper, 1-11 at. % niobium and 2-12 at. % cobalt, wherein the thin film metallic glass has a surface energy of 26.9 mN/m and coefficient of friction of 0.07.

2. The medical injection needle coated with thin film metallic glass of claim 1, wherein the needle body has a tube, and a surface of the tube is coated with the thin film metallic glass.

3. The medical injection needle coated with thin film metallic glass of claim 2, wherein a material of the needle body is selected from a system consisting of titanium, titanium alloy, aluminium, aluminium alloy, copper, copper alloy, iron, iron alloy, gold, gold alloy and steel.

4. The medical injection needle coated with thin film metallic glass of claim 1, wherein the thin film metallic glass has a chemical formula of $Ti_{40}Zr_{10}Cu_{37}Nb_7Co_7$.

5. The medical injection needle coated with thin film metallic glass of claim 4, wherein the thin film metallic glass has a hardness larger than 700 HV.

6. The medical injection needle coated with thin film metallic glass of claim 4, wherein the thin metallic glass film has a thickness ranging from 50 nm to 200 nm.

* * * * *